(12) United States Patent
Nakazawa et al.

(10) Patent No.: US 7,648,240 B2
(45) Date of Patent: Jan. 19, 2010

(54) OPHTHALMIC APPARATUS

(75) Inventors: Naoki Nakazawa, Tokyo (JP); Koji Nakajima, Tokyo (JP); Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 12/052,406

(22) Filed: Mar. 20, 2008

(65) Prior Publication Data
US 2008/0231806 A1  Sep. 25, 2008

(30) Foreign Application Priority Data
Mar. 22, 2007  (JP) .............................. 2007-074327

(51) Int. Cl.
*A61B 3/10* (2006.01)
(52) U.S. Cl. ...................... 351/212; 351/205
(58) Field of Classification Search .................. 351/205, 351/212, 247
See application file for complete search history.

(56) References Cited

U.S. PATENT DOCUMENTS
6,224,213 B1 * 5/2001 Kobayashi .................. 351/212

FOREIGN PATENT DOCUMENTS
JP    3497006 B2    11/2003

* cited by examiner

*Primary Examiner*—Huy K Mai
(74) *Attorney, Agent, or Firm*—Brinks Hofer Gilson & Lione

(57) ABSTRACT

An ophthalmic apparatus comprises a projection system in which a pattern member is provided with a predetermined pattern for measuring the shape of the cornea of an eye of a subject, the predetermined pattern is thereby projected on the cornea of the eye of the subject, and an optical observation system in which light flux having a shape of the predetermined pattern emitted from the projection system is reflected at the cornea of the eye of the subject, the eye of the subject is observed by the light reflected by the cornea. A surface at the eye of the subject side of the pattern member is coated with a paint having a filtering property that transmits infrared light and blocks visible light.

4 Claims, 6 Drawing Sheets

OPHTHALMIC APPARATUS

REFERENCE TO THE RELATED APPLICATIONS

This application claims priority under 35 U.S.C. §119 to Japanese Patent Application No. JP2007-074327 filed Mar. 22, 2007, the entire content of which is hereby incorporated by reference.

BACKGROUND

1. Technical Field

The present invention relates to an ophthalmic apparatus for measuring the shape of the cornea of the eye of a subject.

2. Background Information

Conventionally, in an ophthalmic apparatus for precisely measuring the shape of the cornea, concentric light transmitting portions, that is, light transmitting ring patterns (a placido pattern) are provided to a flat pattern plate, and plural light sources are arranged along the light transmitting ring pattern on a holding plate behind the pattern plate. The light source emits infrared light. This is because infrared light does not cause pupil contraction of the eye of the subject which would occur if a light transmitting ring pattern were projected in visible light.

A filter is located between the pattern plate and the subject on a base material, such as a resin that transmits infrared light and blocks visible light, so that the subject will not see the light transmitting ring pattern projected on the cornea. This configuration is effective to prevent instrument myopia caused by seeing at the light transmitting ring pattern at a short distance. In addition to the ophthalmic apparatus for measuring the shape of the cornea having a filter to block visible light, an ophthalmic apparatus having a plurality of functions, such as an ophthalmic apparatus for measuring the shape of the cornea and the accommodation ability of the eye, and an ophthalmic apparatus for measuring the shape of the cornea and the aberration of optical properties of the eyeball, may also have a filter for blocking visible light.

A flat pattern plate is modified to have a cup shape or a cone shape so as to reduce the size of the ophthalmic apparatus. In the case of a pattern plate having a cup shape or a cone shape, when a filter having a flat shape is disposed between the pattern plate and a subject and is disposed in the vicinity of the subject, the filter may come into contact with the subject. Therefore, the filter is also formed into a cup shape or a cone shape.

In an ophthalmic apparatus having such a structure, light emitted from a light source is converted to a light flux having a shape of plural concentric light transmitting ring patterns, and the light flux is projected onto the cornea of the eye of a subject. Then, the shape of the reflected light of the cornea of the eye of the subject with the concentric light transmitting ring patterns is compared with a shape of the projected pattern so as to observe the difference, and the shape of the cornea is measured from the differences of the shapes (for example, see Japanese Patent No. 3497006).

In a conventional ophthalmic apparatus, a filter that transmits infrared light but blocks visible light is disposed between a pattern plate and a subject, whereby the pattern plate and the filter are required to have the same shape, and the structure is complicated. Moreover, a filter must be disposed between a pattern plate and a subject, and the working distance of an ophthalmic apparatus is thereby somewhat short.

BRIEF SUMMARY

An object of the present invention is to provide a device using a method by which a subject is prevented from seeing a predetermined pattern for projecting on a cornea, and by which the eye of the subject can be measured by a minimum structure without causing instrument myopia and without regard to the shape of a pattern member for forming the predetermined pattern.

The invention according to claim 1 provides an ophthalmic apparatus comprising a projection system and an optical observation system. In the projection system, a pattern member is provided with a predetermined pattern for measuring the shape of the cornea of the eye of a subject, and the predetermined pattern is thereby projected on the cornea of the eye of the subject. In the optical observation system, light flux having the form of the predetermined pattern emitted from the projection system is reflected at the cornea of the eye of the subject, and the eye of the subject is observed by the light reflected by the cornea. A surface at the eye of the subject side of the pattern member is coated with a paint having a filtering property that transmits infrared light and blocks visible light.

It should be noted that infrared light used in an ophthalmic apparatus is transmitted so as to reach an eye of the subject at a light intensity required for measurement. Specifically, a transmission rate of infrared light used in an ophthalmic apparatus is 80% or higher. On the other hand, visible light is blocked so that an opposite side of the coated surface of the pattern member is invisible (or is dimly illuminated). Specifically, the transmission rate of visible light is 10% or less.

In the invention according to claim 1, the surface of the pattern member is coated with a paint having a filtering property that transmits infrared light and blocks visible light, whereby a subject cannot see the predetermined pattern for projecting on the cornea. Moreover, the eye of the subject can be measured by using a minimum structure without causing instrument myopia and without regard to the shape of the pattern member for forming a predetermined pattern.

In the invention defined in claim 2 according to claim 1, the pattern member has an optical axis of the optical observation system as a center, and it is formed with a first surface and a second surface. The first surface is separate from the eye of the subject when it is near the optical axis of the optical observation system, and the second surface gradually rises toward the eye of the subject side when it is separate from the optical axis of the optical observation system. The first surface and the second surface at the eye of the subject side of the pattern member are coated with a paint having a filtering property that transmits infrared light and blocks visible light.

In the invention according to claim 2, the surface of the pattern member is coated with a paint having a filtering property that transmits infrared light and blocks visible light, whereby the subject cannot see the predetermined pattern for projecting on the cornea. Moreover, the shape of the cornea can be measured by using a minimum structure without causing instrument myopia and without regard to the shape of the pattern member for forming a predetermined pattern.

In the invention defined in claim 3 according to claim 2, the first surface is formed so as to cover the nose area of the subject in a condition in which the eye of the subject is aligned with the optical axis of the optical observation system.

In the invention according to claim 3, the first surface is formed so as to cover the nose area of the subject, thereby preventing the nose area of the subject from contacting the pattern member. For example, in a case in which both eyes of a subject are measured, the nose area of the subject, which is the portion nearest to the ophthalmic apparatus, does not contact a pattern member even when the ophthalmic apparatus body moves right or left with respect to the subject.

In the invention defined in claim 4 according to claim 2, the second surface rises toward the subject side at an inclined angle of approximately 45°.

In the invention according to claim 4, the second surface rises toward the subject side at an inclined angle of approximately 45°, thereby preventing the nose area of the subject from contacting the pattern member, and reducing the size of the ophthalmic apparatus.

According to the present invention, a subject cannot see a predetermined pattern for projecting on the cornea. Moreover, a paint functions as a filter that transmits infrared light and blocks visible light, thereby measuring an eye of the subject by using a minimum structure without causing instrument myopia and without regard to the shape of a pattern member for forming a predetermined pattern.

DETAILED DESCRIPTION OF THE PREFERRED EMBODIMENTS

An example of an ophthalmic apparatus together with an apparatus for measuring the shape of the cornea according to the present invention will be described hereinbelow with reference to the figures.

Figure 1:
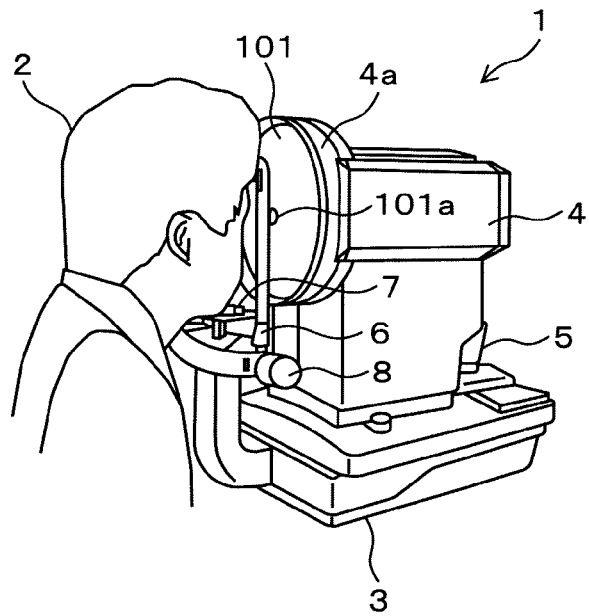
FIG. 1 is a perspective view showing a relationship of an ophthalmic apparatus according to the present invention and a subject.
Figure 2:
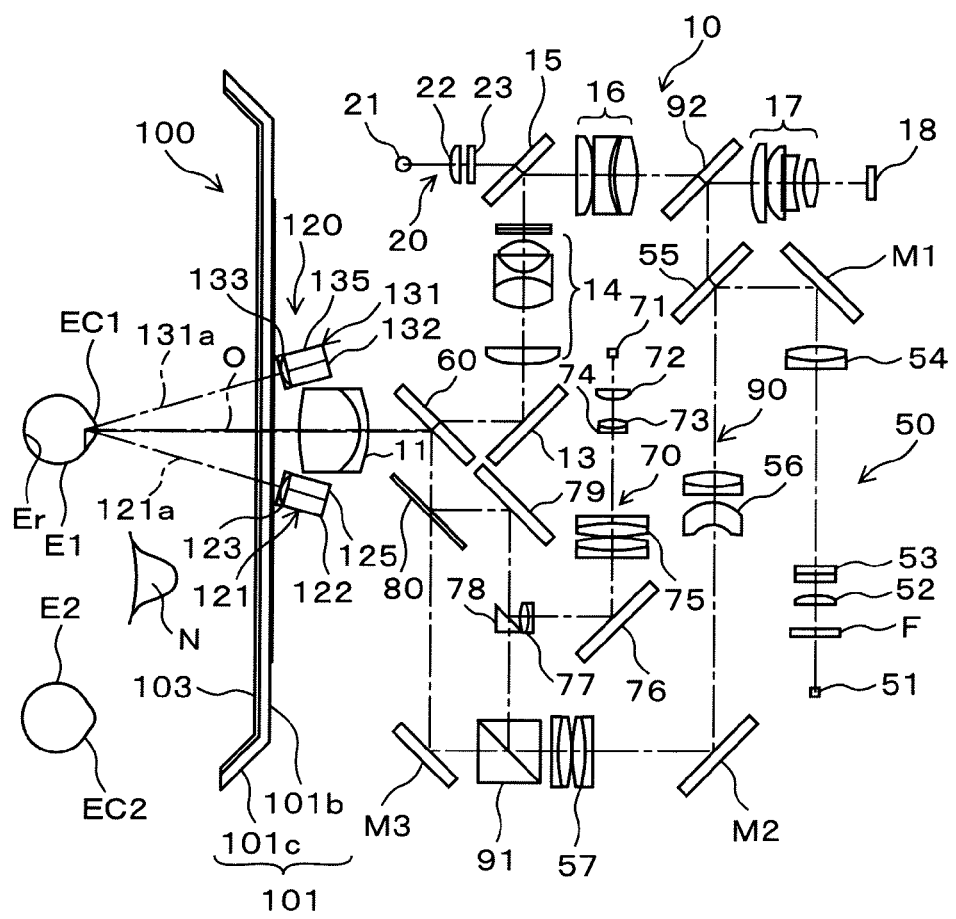
FIG. 2 is an optical layout drawing showing a layout of an optical system of an ophthalmic apparatus.
Figure 3:
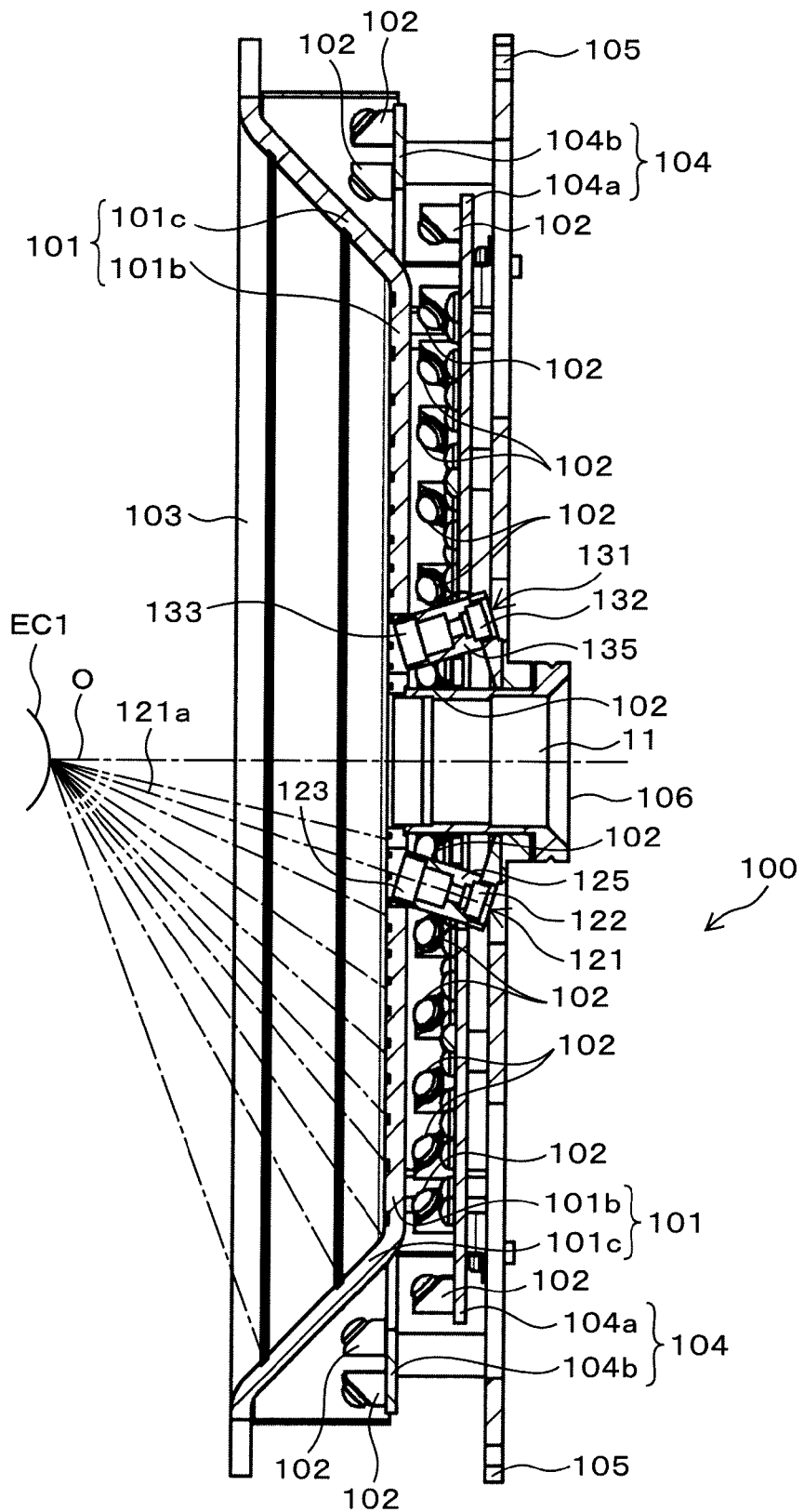
FIG. 3 is a sectional view showing a structure of a placido pattern projecting system.
Figure 4:
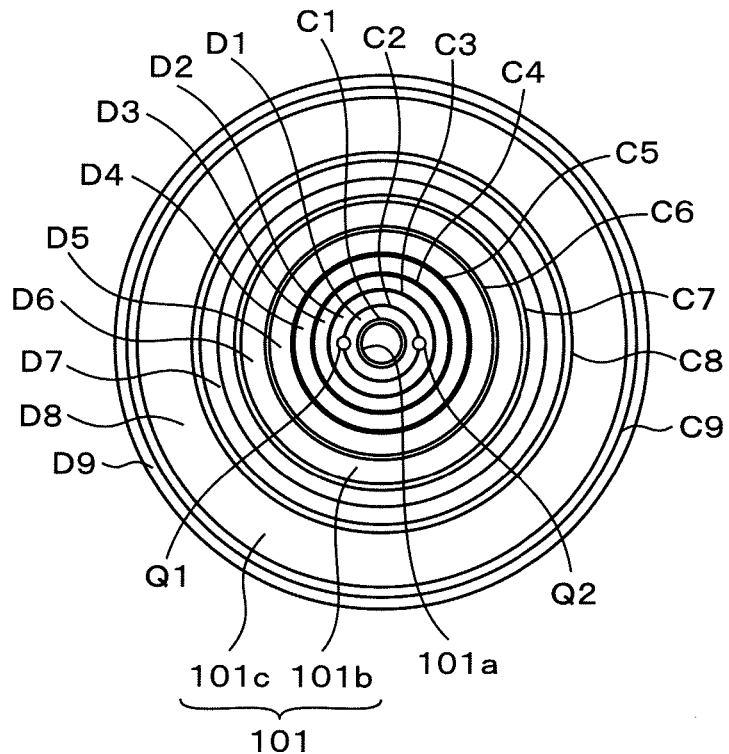
FIG. 4 is a front view showing a pattern portion of a placido pattern projecting system.
Figure 5:
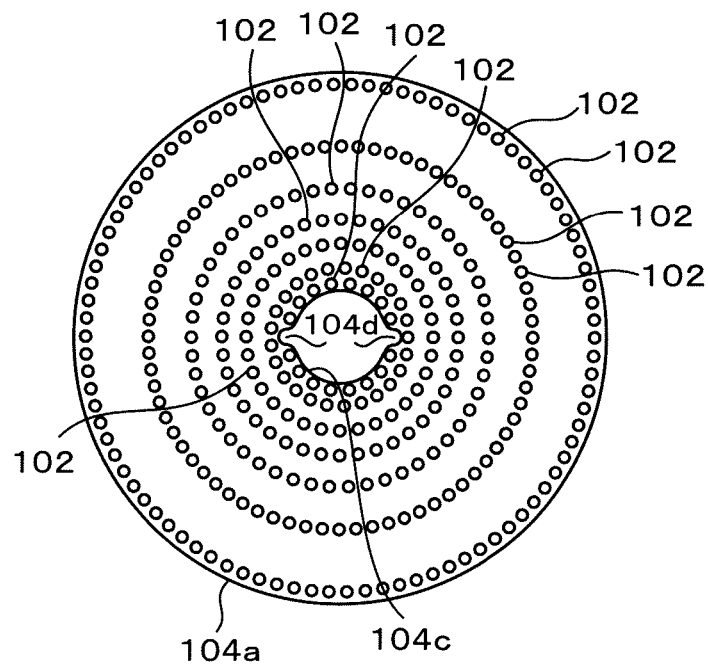
FIG. 5 is a front view of a holding plate showing an arrangement of infrared light-emitting diodes.
Figure 6A:
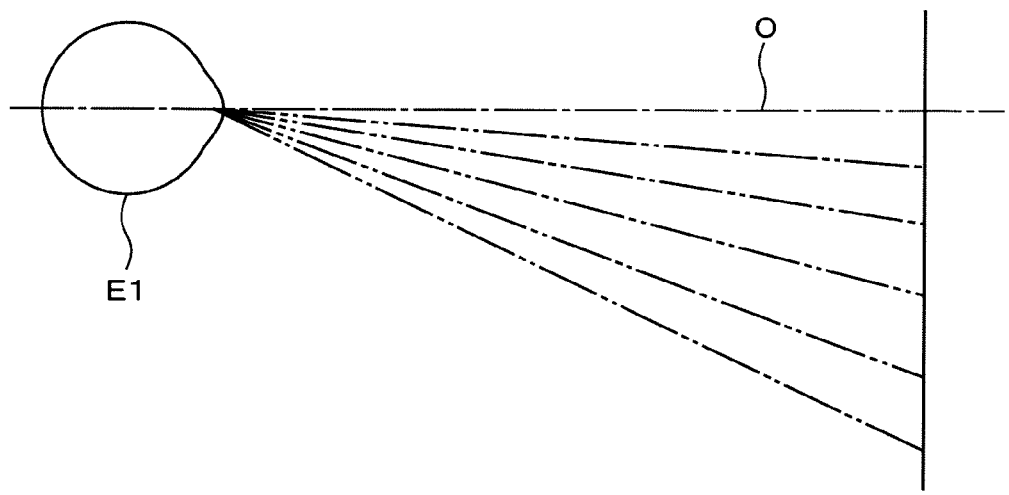
FIGS. 6A and 6B are explanatory drawings showing differences in positions of patterns and differences in sizes of pattern portions due to the shape of the pattern portion.
Figure 6B:
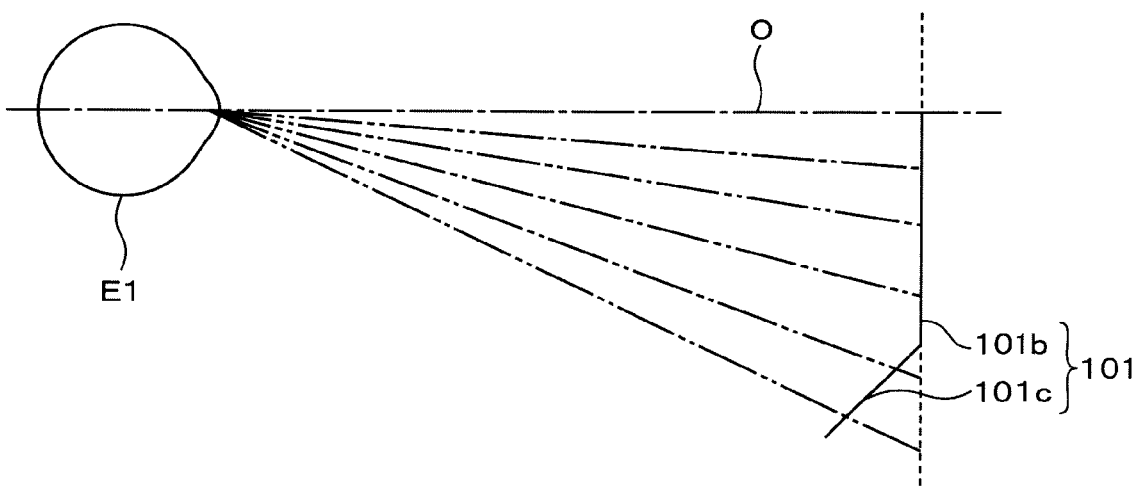
Figures 7A, 7B:
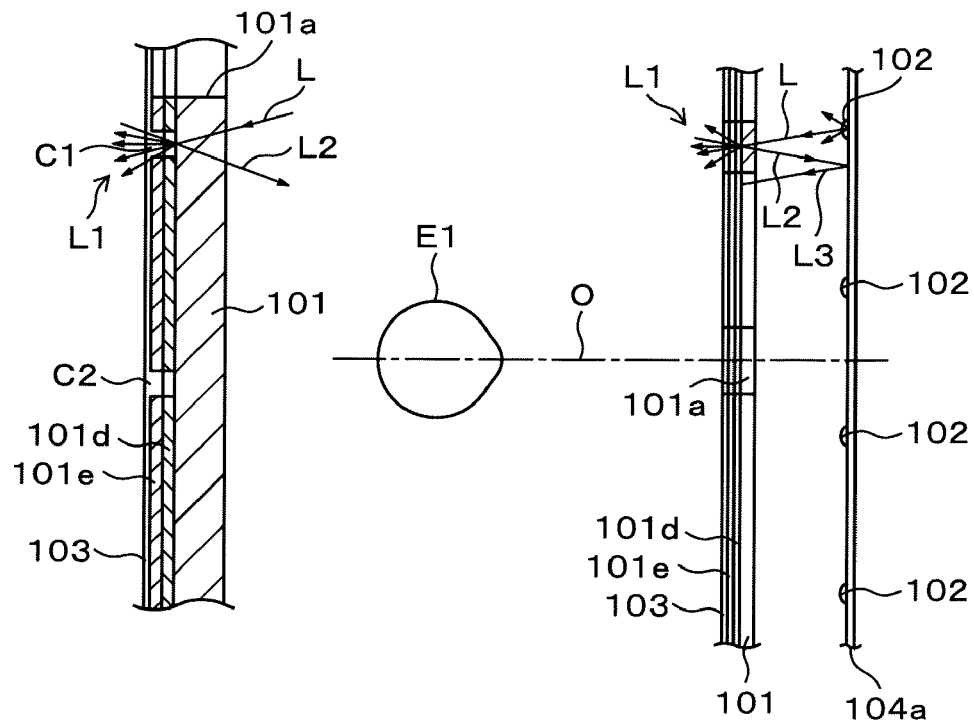
FIGS. 7A and 7B are schematic drawings showing an enlarged portion of a placido pattern projecting system.
Figure 8:
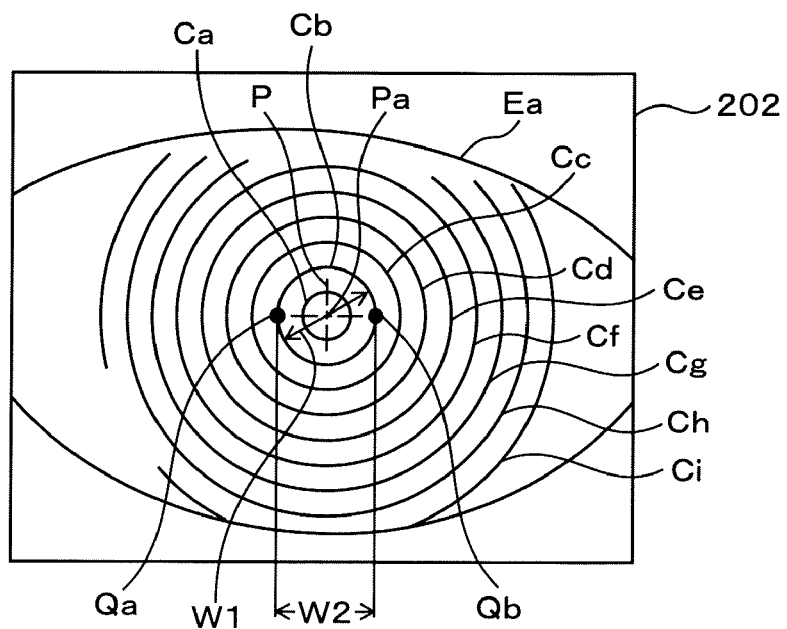
FIG. 8 is an explanatory drawing showing an image displayed on a monitor.
Figure 9:
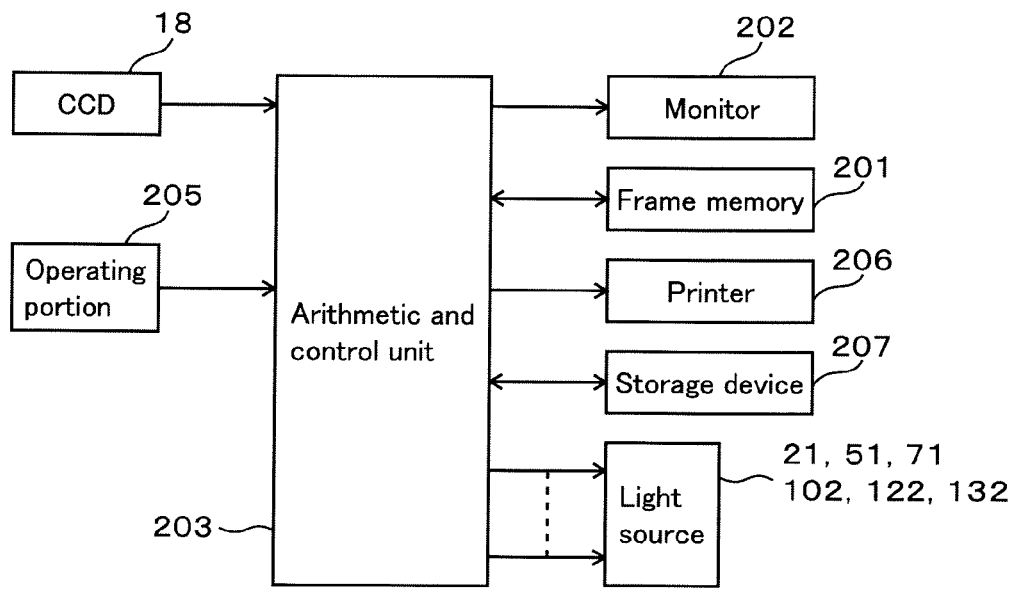
FIG. 9 is a block diagram showing a structure of a control system of an ophthalmic apparatus.
Figure 10:
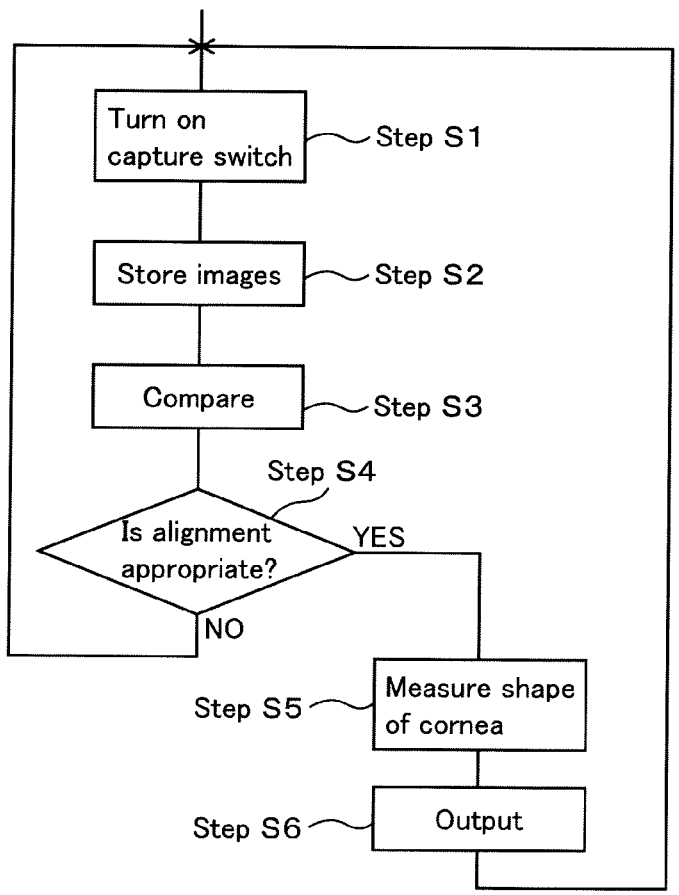
FIG. 10 is a flow diagram showing an operation of an ophthalmic apparatus.

FIG. 1 is a perspective view showing the relationship of an ophthalmic apparatus according to the present invention and a subject. FIG. 2 is an optical layout drawing showing a layout of an optical system of an ophthalmic apparatus. FIG. 3 is a sectional view showing a structure of a placido pattern projecting system. FIG. 4 is a front view showing a pattern portion of a placido pattern projecting system. FIG. 5 is a front view of a holding plate showing an arrangement of infrared light-emitting diodes. FIGS. 6A and 6B are explanatory drawings showing differences in positions of patterns and differences in sizes of pattern portions due to the shape of the pattern portion. FIGS. 7A and 7B are schematic drawings showing portions of a placido pattern projecting system enlarged. FIG. 8 is an explanatory drawing showing an image displayed on a monitor. FIG. 9 is a block diagram showing a structure of a control system of an ophthalmic apparatus. FIG. 10 is a flow diagram showing an operation of an ophthalmic apparatus.

First, a structure of an ophthalmic apparatus 1 will be described.

As shown in FIG. 1, the ophthalmic apparatus 1 comprises a base 3, an apparatus body 4 mounted on the base 3 and movable from front to back and from right to left, a joystick 5 mounted on the apparatus body 4 so as to move the apparatus body 4 from front to back and from right to left, a frame 6 fixed on the front end of the base 3, a jaw rest 7 provided to the frame 6 and movable in a vertical direction, and a handling knob 8 held by the frame 6 so as to move the jaw rest 7 in a vertical direction.

Furthermore, as shown in FIG. 2, the ophthalmic apparatus 1 comprises an anterior eye observing optical system (an optical observation system) 10 for observing an anterior eye of an eye of the subject E1, a fixation target projecting optical system 50 for projecting a fixation target on the eye of the subject E1, a measurement and projection optical system 70 for projecting light on an eyeground Er of the eye of the subject E1 so as to measure the refractive power of the eye, a light receiving optical system 90 for receiving the light reflected at the eyeground Er, a placido pattern projecting system (a projection system) 100 for projecting a placido pattern (a predetermined pattern) on a cornea EC1 of the eye of the subject E1 so as to measure the shape of the cornea, and a parallel light flux projecting optical system 120 for projecting a mark on the cornea EC1 so as to detect a working distance.

The anterior eye observing optical system 10 comprises an objective lens 11, a dichroic mirror 60, a mirror 13, a relay lens 14, a dichroic mirror 15, a relay lens 16, an imaging lens 17, and an area sensor 18 including a CCD for receiving light reflected at the cornea.

Moreover, the anterior eye observing optical system 10 is provided with a scale projecting system 20 for projecting a cross scale image P (see FIG. 8) on the area sensor 18. The scale projecting system 20 comprises a light source 21, a condenser lens 22, and a scale plate 23 formed with a scale (not shown in the figure). Light emitted from the light source 21 is concentrated on the condenser lens 22 and illuminates the scale plate 23, and a cross-shaped light flux is thereby formed. The light flux reaches the imaging lens 17 via the dichroic mirrors 15 and 92, which will be described hereinafter, and it provides a scale image P on the area sensor 18 through the imaging lens 17. Then, the scale image P and the anterior eye are displayed together on the monitor 202 (see FIG. 8).

The fixation target projecting optical system 50 comprises a light source 51, a filter F for blocking infrared light, a condenser lens 52, a fixation target plate 53, a relay lens 54, a mirror M1, a dichroic mirror 55, a relay lens 56, a mirror M2, a relay lens 57, a mirror M3, a dichroic mirror 60, and the objective lens 11. The fixation target plate 53 is positioned with reference to the eyeground Er and is formed with a mark (not shown in the figure) for a fixation target, and the mark is thereby projected on the eyeground Er. The eye of the subject E1 is turned to a predetermined direction and appears fogged by projection of the mark.

The measurement and projection optical system 70 comprises a light source 71, a condenser lens 72, a conical prism 73, a ring aperture plate 74 formed with a ring aperture (not shown in the figure), a relay lens 75, a mirror 76, a relay lens 77, a dichroic mirror 78, a mirror 79, a dichroic mirror 80, a dichroic mirror 60, and the objective lens 11.

The conical prism 73 condenses light, which is emitted from the light source 71 and is concentrated by the condenser lens 72, to the ring aperture of the ring aperture plate 74. The ring aperture plate 74 is positioned with reference to the eyeground Er, and a ring image (not shown in the figure) is projected on the eyeground Er by light flux passing through the ring aperture of the ring aperture plate 74.

Reflected light flux of the ring image projected on the eyeground Er is provided on the area sensor 18 via the objective lens 11, the dichroic mirror 60, the dichroic mirror 80, the mirror 79, the dichroic mirror 78, the dichroic mirror 91, the relay lens 57, the mirror M2, the relay lens 56, the dichroic mirror 55, the dichroic mirror 92, and the imaging lens 17, and a ring image is formed. The refractive power of the eye is calculated from the ring image by an arithmetic and control unit 203, which will be described hereinafter.

The light receiving optical system 90 comprises the objective lens 11, a dichroic mirror 60, a dichroic mirror 80, a mirror 79, dichroic mirrors 78 and 91, a relay lens 57, a mirror M2, a relay lens 56, dichroic mirrors 55 and 92, the imaging lens 17, and the area sensor 18.

As shown in FIG. 3, the placido pattern projecting system 100 comprises a pattern portion (a pattern member) 101, plural infrared light-emitting diodes 102, a visible-light-blocking filter painted layer 103, a holding plate 104, and a unit base 105.

The plural infrared light-emitting diodes 102 are mounted on a first holding plate 104a and a second holding plate 104b at predetermined intervals along rings (light transmitting ring patterns) C1 to C9 which will be described hereinafter. When the placido pattern of the pattern portion 101 is projected on the eye of the subject E1 by the infrared light-emitting diodes 102, the placido pattern is projected by infrared light, whereby the subject does not notice the placido pattern.

In this case, the infrared light used in the ophthalmic apparatus 1 has a wavelength of 950 nm. It should be noted that the wavelength of the infrared light used in the ophthalmic apparatus 1 may be selected from a range of 920 nm to 970 nm.

A white reflective layer (not shown in the figure) is provided on a surface on which the infrared light-emitting diodes 102 of the holding plate 104 fixed on the unit base 105 is provided. The reflective layer reflects infrared light to the eye of the subject E1. A printing method of a white serigraph for explanatory portions is used for the holding plate 104, whereby the reflective layer is easily formed by coating a white paint on the holding plate 104.

The pattern portion 101 is formed by a diffuser that can transmit and diffuse light, and it includes a disk surface (a first surface) 101b and a circular surface (a second surface) 101c as shown in FIGS. 2 to 4. The pattern portion 101 is attached to a cylindrical portion 4a of the front end of the apparatus body 4 as shown in FIG. 1. As shown in FIG. 2, under conditions in which an eye of the subject (an eye) E1 is aligned with an optical axis (the light source of the optical observation system) O of the ophthalmic apparatus 1, the pattern portion 101 is formed so that a portion near the edge thereof faces an eye of the subject (the other eye) E2. Therefore, both eyes E1 and E2 of a subject 2 face the pattern portion 101.

As shown in FIGS. 2 to 4, the disk surface 101b of the pattern portion 101 has an optical axis O as a center and is formed into an approximately flat disk shape, and a portion thereof in proximity of the optical axis O is provided at a distance from the eye of the subject E1 of the subject 2.

In addition, the disk surface 101b is required to have a size that covers the nose (nose area) N of the subject 2 under conditions in which the eye of the subject E1 is aligned with the optical axis O, and it preferably has a diameter of approximately 139 mm. If the diameter of the disk surface 101b is approximately 139 mm, the nose N of a subject 2 is prevented from coming into contact with the pattern portion 101 even when the subject 2 has a large nose N and when there is a substantial distance between an eye of the subject E1 and the other eye of the subject E2.

Thus, the disk surface 101b is formed so as to cover the nose N of the subject 2, whereby contact of the nose N of the subject 2 with the pattern portion 101 can be avoided. For example, in a case in which both eyes E1 and E2 of a subject 2 are measured, contact of the nose N of the subject 2 with the pattern portion 101 can be avoided even when the apparatus body 4 moves from right to left with respect to the subject 2.

As shown in FIGS. 2 to 4, the circular surface 101c of the pattern portion 101 is formed into an approximately circular shape, and it gradually rises toward the eye of the subject E1 side. That is, the circular surface 101c gradually rises toward the eye of the subject E1 side as the distance from the optical axis O increases. Accordingly, the pattern portion 101 is formed into an approximately dish shape. In this case, the circular surface 101c of the pattern portion 101 is required to gradually rise toward the eye of the subject E1 side, and in the embodiment, it rises toward the eye of the subject E1 side at an inclined angle of approximately 45°.

Thus, the circular surface 101c gradually rises toward the side of the eye E1 of the subject 2, thereby allowing a reduction in the size of ophthalmic apparatus 1 as shown in FIG. 6B compared to a case in which the pattern portion has a flat shape as shown in FIG. 6A. Specifically, when the incline of the circular surface 101c is approximately 45°, contact of the nose N of the subject 2 with the pattern portion 101 can be avoided, and the ophthalmic apparatus 1 can be reduced in size.

In this case, the pattern portion 101 is not limited to have an approximately dish shape, and it may have a cup shape, a cone shape, or a flat shape.

As shown in FIG. 4, the pattern portion 101 has a circular hole 101a at the center thereof and is provided with rings C1 to C9, which are nine concentric patterns for measuring the shape of the cornea, around the hole 101a. That is, the disk surface 101b and the circular surface 101c are provided with patterns for measuring the shape of the cornea.

As shown in FIG. 4 and FIGS. 7A and 7B, plural light blocking portions D1 to D9 consist of a white reflective layer 101d and a black layer 101e, and they are concentrically formed on the surface of the pattern portion 101 at intervals. Each ring C1 to C9 is formed at each interval between the adjacent light blocking portions D1 to D9. That is, the rings C1 to C9 are portions that are not coated by paint for forming the white reflective layer 101d and the black layer 101e.

Accordingly, infrared light, which is infrared light emitted from the plural infrared light-emitting diodes 102 and goes to the rings C1 to C9, is repeatedly diffused and reflected by an effect of the light blocking portions D1 to D9 and the holding plate 104, as shown by L, L1, and L2 in FIGS. 7A and 7B. The diffusion and the reflection function will be described by the ring C1 and one infrared light-emitting diode 102. That is, when light flux L emitted from the infrared light-emitting diode 102 goes to the ring C1 through the pattern portion 101 that is a diffuser, most of the light flux L is transmitted through the ring C1 as diffused light L1, and the rest is reflected to the holding plate 104 as reflected light L2.

After the reflected light L2 is reflected at the holding member 104 as reflected light L3, it is reflected between the white reflective layer 101d and the holding plate 104 many times and is projected to the eye of the subject E1 side from any of the rings C1 to C9. Therefore, light emitted from the infrared light-emitting diode 102 is efficiently used for projecting a placido pattern, and the placido pattern can be illuminated by uniform infrared light.

As shown in FIG. 4, the pattern portion 101 is formed with two circular holes Q1 and Q2 which are aligned in a horizontal direction, and light flux for positioning the optical axis O passes through the holes. The holes Q1 and Q2 are portions not coated by paint for forming the white reflective layer 101d and the black layer 101e, which is the same as the case of the ring pattern.

Moreover, as shown in FIGS. 7A and 7b, the pattern portion 101 is formed with a visible-light-blocking filter painted layer 103 on the surface of the black layer 101e and the rings C1 to C9. That is, a visible-light-blocking filter painted layer 103 is formed between the pattern portion 101 and the eye of the subject E1.

The visible-light-blocking filter painted layer 103 is a painted layer that transmits infrared light and blocks visible light. That is, the visible-light-blocking filter painted layer 103 is a painted layer that transmits infrared light and blocks visible light, primarily by absorbing visible light. The visible-light-blocking filter painted layer 103 is formed by coating a paint, which transmits infrared light and absorbs visible light, on the surface of the pattern portion 101 formed with the white reflected layer 101d and the black layer 101e. The visible-light-blocking filter painted layer 103 is a painted layer that transmits infrared light used in the ophthalmic apparatus 1 by 80% or more and blocks visible light by 90% or more.

As a paint for forming the visible-light-blocking filter painted layer 103, such as a filtering resin, that blocks visible light, one produced by Dai Nippon Toryo Co., Ltd. may be mentioned. The thickness of the visible-light-blocking filter painted layer 103 is approximately 2.5 μm in this embodiment. It should be noted that the thickness of the visible-light-blocking filter painted layer 103 may be appropriately selected.

The visible-light-blocking filter painted layer 103 is formed between the eye of the subject E1 and the pattern portion 101, whereby the placido pattern of the pattern portion 101 cannot be seen by external light such as light from indoor lighting. Moreover, the visible-light-blocking filter painted layer 103 absorbs visible light, thereby avoiding reflection of subject 2 in the visible-light-blocking filter painted layer 103.

Therefore, when the refractive power of the eye is measured, the placido pattern and the image of the subject 2 do not attract the attention of the subject 2, and an accommodation effect of the eye of the subject E1 does not occur, whereby the refractive power of the eye can be precisely measured.

The parallel light flux projecting optical system 120 has holes Q1 and Q2 formed in the pattern portion 101, and a pair of parallel light projecting units 121 and 131 (see FIG. 2) arranged on the same horizontal plane as that of the holes. The parallel light projecting unit 121 comprises an infrared light-emitting diode 122 and a projecting lens 123 in a case 125, and the parallel light projecting unit 131 comprises an infrared light-emitting diode 132 and a projecting lens 133 in a case 135. The projecting lens 123 transforms infrared light emitted from the infrared light-emitting diode 122 into parallel light flux and projects it through the hole Q1. The projecting lens 133 transforms infrared light emitted from the infrared light-emitting diode 132 into parallel light flux and projects it through the hole Q2.

An optical axis 121a of the parallel light projecting unit 121 passes through the hole Q1 and faces a cornea EC1 of an eye of the subject E1, and an optical axis 131a of the parallel light projecting unit 131 passes through the hole Q2 and faces the cornea EC1 of the eye of the subject E1. The parallel light fluxes of the projecting lenses 123 and 133 projects the holes Q1 and Q2 from an infinite distance to the cornea EC1 of the eye of the subject E1, respectively. That is, the parallel light flux is projected on the cornea EC1 of the eye of the subject E1 through the holes Q1 and Q2 from a distance different from the distance between the cornea EC1 and the pattern portion 101.

The case 125 of the parallel light projecting unit 121 is inserted into a concave portion 104d of a hole 104c formed in the center of the holding plate 104, and it is fixed to a lens tube portion 106 by screws (not shown in the figure). The case 135 of the parallel light projecting unit 131 is also fixed to the lens tube portion 106 in the same way as that of the case 125.

FIG. 9 shows a frame memory 201 for storing images received by an area sensor 18, a monitor 202 for displaying images received by the area sensor 18, and an arithmetic and control unit 203. The arithmetic and control unit 203 functions as a device for calculating the shape of the cornea from each ring image Ca to Ci (see FIG. 8) stored in the frame memory 201, a device for detecting a working distance of the apparatus body 4 from a ratio of a diameter W1 of the ring image Cb and a distance W2 between bright points Qa and Qb, and a device for correcting the shape of the cornea based on the working distance.

An apparatus for measuring the shape of the cornea comprises a placido pattern projecting system 100, a parallel light flux projecting optical system 120, an anterior eye observing optical system 10, and an arithmetic and control unit 203.

In addition, the arithmetic and control unit 203 controls a printer 206, a storage device 207, light sources 21, 51, 71, 102, 122, and 132, and the like based on an operation of an operating portion 205. The arithmetic and control unit 203 calculates a refractive power of eye from a ring image projected on an eyeground Er.

Next, an operation of the above ophthalmic apparatus 1 will be described.

The light source 102 of the placido pattern projecting system 100 and the infrared light-emitting diodes 122 and 132 of the parallel light flux projecting optical system 120 are lit by controlling the operating portion 205. Moreover, the light source 21 of the scale projecting system 20 is lit.

After the light source 102 is lit, a ring-shaped light flux of infrared light is emitted from the rings C1 to C9 of the pattern portion 101 through the visible-light-blocking filter painted layer 103. The ring-shaped light flux is projected on the cornea EC1 of the eye of the subject E1, and reflected images of C1 to C9 are thereby formed.

Similarly, infrared light emitted from the infrared light-emitting diodes 122 and 132 is transformed into parallel light fluxes by projecting lenses and passes through the holes Q1 and Q2, respectively, and is projected on the cornea EC1 of the eye of the subject E1. As a result, bright points Qa and Qb are formed by the reflected light of the cornea EC1.

Light fluxes of reflected images of rings and a mark reflected at the cornea EC1 of the eye of the subject E1 and an anterior eye image are provided on the area sensor 18 via the objective lens 11, the dichroic mirror 60, the mirror 13, the relay lens 14, the dichroic mirror 15, the relay lens 16, the dichroic mirror 92, and the imaging lens 17. Then, as shown in FIG. 8, the reflected image of rings Ca to Ci and the bright points Qa and Qb are displayed together with the anterior eye image Ea on the monitor 202.

Moreover, a scale image is provided on the area sensor 18 by lighting the light source 21 of the scale projecting system 20, and a scale image P is thereby displayed on the monitor 202.

The operator performing the examination aligns the X direction and the Y direction by moving the apparatus body 4 from right to left and up and down while viewing the scale image P and the reflected image of ring Ca displayed on the monitor 202, so that an intersection point Pa of the scale image P is centered in the reflected image of ring Ca. Moreover, alignment in the Z direction is adjusted by moving the apparatus body 4 from front to back so that the bright points Qa and Qb approximately coincide with the reflected image Cb of the ring.

Since the bright points Qa and Qb are projected by parallel light flux, a distance W2 between the bright points Qa and Qb is fixed regardless of a distance in the Z direction of the apparatus body 4. On the other hand, a diameter W1 of the reflected image Cb of the ring depends on the distance in the Z direction. Therefore, the alignment in the Z direction can be adjusted by comparing the distance W2 between the bright points Qa and Qb and the diameter W1 of the reflected image Cb of the ring, and the working distance is thereby determined.

Thus, the scale image P is displayed on the monitor 202, and the alignment can be adjusted simply by looking at the scale image P, whereby the alignment is easily adjusted.

After the alignments are adjusted, as shown in FIG. 10, when a measuring switch (not shown in the figure) of the operating portion 205 is pushed (step S1), an image shown in FIG. 8 is stored in the frame memory 201 in a step S2.

In the arithmetic and control unit 203, the ratio of the diameter W1 of the reflected image Cb of the ring and the distance W2 between the bright points Qa and Qb stored in the frame memory 201 is determined, and a working distance of the apparatus body 4 is calculated from the ratio. Then, a difference in the working distance and a predetermined working distance, that is, an error in the alignment in the Z direction is calculated (step S3). It is then determined whether or not the error is within a predetermined range in a step S4. If the error is outside the predetermined range, the shape of the cornea is measured by using the reflected images Ca to Ci of the ring stored in the frame memory 201, and the shape of the cornea is corrected according to the above error (step S5). Accordingly, the shape of the cornea can be accurately measured by the correction even when the alignment in the Z direction is not precisely adjusted.

The shapes of the cornea before and after the correction and the working distance are displayed on the monitor 202 and are printed out by a printer 206, and these data and the image shown in FIG. 8 are stored in the storage device 207 (step S6).

Thus, even when the alignment in the Z direction is not precisely adjusted, the error in the alignment can be measured, and the measured shape of the cornea may be corrected based on the error so as to calculate an accurate shape of the cornea. Therefore, the acceptable range of the alignment can be set to be large even when the working distance is short, and the shape of the cornea can be accurately measured.

When the refractive power of the eye is measured, the light source 51 of the fixation target projecting optical system 50 is lit so that the eye of the subject E1 looks in a predetermined direction and appears fogged. Then, the light source 71 of the measurement and projection optical system 70 is lit so as to project an image of a ring (not shown in the figure) on the eyeground Er. The image of the ring is provided on the area sensor 18 via the objective lens 11, the dichroic mirror 60, the dichroic mirror 80, the mirror 79, the dichroic mirror 78, the dichroic mirror 91, the relay lens 57, the mirror M2, the relay lens 56, the dichroic mirror 55, the dichroic mirror 92, and the imaging lens 17, so as to calculate the refractive power of the eye from the image of ring by the arithmetic and control unit 203.

After one eye of the subject E1 is measured, in order to measure the other eye of the subject E2, the apparatus body 4 is moved to the left with respect to the subject 2 so that the optical axis O is aligned with the eye of the subject E2. In this case, the pattern portion 101 does not contact the nose N of the subject 2. Then, the other eye of the subject E2 is measured by the above process.

In the above embodiment, the placido pattern projecting system 100 is provided together with a device for measuring the refractive power of the eye. For example, the placido pattern projecting system 100 may be provided together with an ophthalmic apparatus such as a fundus camera, and an ophthalmic apparatus for measuring an aberration of the optical system of the eyeball may be provided together with an apparatus for measuring only the shape of the cornea by using a placido pattern. Moreover, an ophthalmic apparatus for measuring the accommodation ability of eye may be provided together with the apparatus for measuring the shape of the cornea, or an optical system for measuring refractive power of the eye may be removed from the above ophthalmic apparatus so as to obtain an apparatus for measuring only the shape of the cornea by using placido pattern.

The scale image P is stored in the frame memory 201 in the above embodiment, and the light source 21 of the scale projecting system 20 may be turned off when the measuring switch is pushed so as not to store the scale image P in the frame memory 201. In this case, the scale image P does not interfere with calculation of the shape of the cornea and the working distance. The holes Q1 and Q2 are projected by parallel light flux from an infinite distance to the cornea EC1 of the eye of the subject E1 in the embodiment, and they may be projected by light other than the parallel light flux from a position other than the pattern portion 101 to the cornea EC1 of the eye of the subject E1.

In the above embodiment, an image is stored in the frame memory 201 so as to calculate the shape of the cornea and the working distance when a measuring switch is pushed. Images may be continuously scanned so as to calculate a real-time working distance by not pushing the measuring switch, and the shape of the cornea may be calculated and be output only when the working distance is within an appropriate range.

The present invention may be used in an improved technique for an ophthalmic apparatus in which a predetermined pattern is projected on a cornea, and light reflected by the cornea is received so as to measure the shape of the cornea.

The invention claimed is:

1. An ophthalmic apparatus comprising:
    a projection system in which a pattern member is provided with a predetermined pattern for measuring the shape of a cornea of an eye of a subject, the predetermined pattern being thereby projected on the cornea of the eye of the subject; and
    an optical observation system in which light flux having a shape of the predetermined pattern emitted from the projection system is reflected at the cornea of the eye of the subject, the eye of the subject being observed by the light reflected by the cornea,
    a measurement and projection optical system for projecting a ring image on an eye ground of the eye of the subject: and
    an arithmetic unit functioning for calculating the shape of the cornea of the eye of the subject based on the light reflected by the cornea, the arithmetic unit functioning for calculating a refractive power of the eye based on the ring image projected on the eye ground of the eye of the subject, wherein the pattern member has a surface at a side of the eye of the subject, and the surface is coated with a paint having a filtering property that transmits infrared light by 80% or more and absorbs visible light so as to block the visible light by 90% or more, whereby the subject is prevented from seeing the predetermined pattern of the pattern member and the refractive power of the eye is precisely measured without causing an accommodation effect of the eye of the subject.

2. The ophthalmic apparatus according to claim 1, wherein the pattern member has an optical axis of the optical observation system as a center and is formed by a first surface and a second surface, the first surface is separate from the eye of the subject when it is near the optical axis of the optical observation system, the second surface gradually rises toward the eye of the subject side when it is separate from the optical axis of the optical observation system; and wherein the first surface and the second surface at the eye of the subject side of the pattern member are coated with the paint having a filtering property that transmits infrared light and blocks visible light.

3. The ophthalmic apparatus according to claim 2, wherein the first surface is formed so as to cover the nose area of the subject when the eye of the subject is aligned with the optical axis of the optical observation system.

4. The ophthalmic apparatus according to claim 2, wherein the second surface rises toward the subject side at an inclined angle of approximately 45°.

\* \* \* \* \*